(12) United States Patent
Dott et al.

(10) Patent No.: US 8,277,822 B2
(45) Date of Patent: Oct. 2, 2012

(54) BOTULINUM TOXIN TREATMENT

(75) Inventors: Chris Dott, Berkshire (GB); John Batchelor, Berkshire (GB); Pierre Bernard D'Arbigny, Courbevoie (FR); Roland Cherif-Cheikh, Barcelona (ES)

(73) Assignee: Ipsen Biopharm Limited, Wrexham (GB)

( * ) Notice: Subject to any disclaimer, the term of this patent is extended or adjusted under 35 U.S.C. 154(b) by 324 days.

(21) Appl. No.: 12/155,104

(22) Filed: May 29, 2008

(65) Prior Publication Data
US 2009/0028907 A1 Jan. 29, 2009

Related U.S. Application Data

(63) Continuation of application No. 10/581,671, filed as application No. PCT/GB2004/004770 on Nov. 12, 2004, now abandoned.

(30) Foreign Application Priority Data

Dec. 4, 2003 (GB) .................................. 0328060.9

(51) Int. Cl.
*A61K 39/08* (2006.01)
*A61P 13/10* (2006.01)

(52) U.S. Cl. .................................................... 424/239.1
(58) Field of Classification Search .................. None
See application file for complete search history.

(56) References Cited

U.S. PATENT DOCUMENTS

| | | | |
|---|---|---|---|
| 5,236,956 A | 8/1993 | Sjögren et al. | |
| 5,437,291 A | 8/1995 | Pasricha et al. | |
| 6,306,423 B1 * | 10/2001 | Donovan et al. | |
| 6,630,570 B1 | 10/2003 | Licha et al. | |
| 6,638,246 B1 | 10/2003 | Naimark et al. | 604/103 |
| 7,226,605 B2 | 6/2007 | Suskind et al. | |
| 2002/0099356 A1 | 7/2002 | Unger et al. | 604/501 |
| 2003/0108597 A1 | 6/2003 | Chancellor et al. | |
| 2003/0203030 A1 | 10/2003 | Ashton et al. | |
| 2003/0211975 A1 | 11/2003 | Unger | 514/2 |

FOREIGN PATENT DOCUMENTS

| | | |
|---|---|---|
| JP | 05-064661 | 3/1993 |
| WO | WO 96/22806 | 8/1996 |
| WO | WO99/03483 | 1/1999 |
| WO | WO 99/03483 | 1/1999 |
| WO | WO 02/43796 | 6/2002 |
| WO | WO2004/010934 | 2/2004 |

OTHER PUBLICATIONS

Dykstra et al, Arch Phys Med Rehabil vol. 71, Jan. 1990, pp. 24-26, Treatment of Detrusor-Sphincter Dyssynergia with Botulinum.
Yokoyama et al, ACTA Med vol. 56, No. 6, 2002, pp. 271-277, Botulinum Toxin Treatment of Urethral and Bladder Dysfunction.
Ranan DasGupta & Clare J. Fowler, Bladder, Bowel and Sexual Dysfunction in Multiple Sclerosis: Management Strategies, Drug 2003, vol. 63, No. 2, pp. 153-166.

* cited by examiner

*Primary Examiner* — Michele C. Flood
(74) *Attorney, Agent, or Firm* — Jacobson Holman PLLC

(57) ABSTRACT

A liquid or semi-solid formulation of botulinum toxin for the preparation of a medicament intended to treat a disorder characterized by bladder spasms (e.g. urinary incontinence due to unstable bladder or unstable detrusor sphincter, voiding complications due to detrusor overactivity or unstable detrusor sphincter, urinary retention secondary to spastic sphincter or hypertrophied bladder neck and neurogenic bladder dysfunction secondary to Parkinson's disease, spinal cord injury, stroke or multiple sclerosis or characterized by a spasm reflex), wherein said medicament is for administration by infusion into the bladder or by other methods that do not involve injection into the bladder wall.

9 Claims, No Drawings

BOTULINUM TOXIN TREATMENT

This application is a Continuation application of U.S. patent application Ser. No. 10/581,671, filed Apr. 2, 2007 now abandoned, which is a nationalization of PCT/GB04/004770 filed Nov. 12, 2004 and published in English.

The present invention relates to the use of botulinum toxin for the preparation of a medicament intended to topically treat urinary disorders and notably spastic bladder.

The anaerobic, gram positive bacterium *Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food tins, which are the cause of many of the cases of botulism. The effects of botulism typically appear 18 to 36 hours after eating the foodstuffs infected with a Clostridium botulinum culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of a commercially available botulinum toxin type A (purified neurotoxin complex) correspond to the $LD_{50}$ in mice.

Seven immunologically distinct botulinum neurotoxins have been characterized, these being respectively botulinum neurotoxin serotypes A, B, $C_1$, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the $LD_{50}$ in mice, than botulinum toxin type B. Additionally, botulinum toxin type B has been determined to be nontoxic in primates at a-dose of 480 U/kg which is about 12 times the primate $LD_{50}$ for botulinum toxin type A. Botulinum toxin apparently binds with high affinity to cholinergic motor neurons, is translocated into the neuron and blocks the release of acetylcholine.

Although all the botulinum toxin serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kilodalton (kD) synaptosomal associated protein (SNAP-25), but they target different amino acid sequences within this protein. Botulinum toxin types B, D, F and G act on vesicle-associated protein (V,AMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes.

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 k-D forms. Botulinum toxin types B and $C_1$ are apparently produced as only a 500 kD complex. Botulinum toxin type D is produced as both 300 ka and 500 kD complexes. Finally, botulinum toxin types E and F are produced as only approximately 300 kD complexes. The complexes (i.e. molecular weight greater than about 150 kD) are believed to contain a non-toxin hemaglutinin protein and a nontoxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

Botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level. High quality crystalline botulinum toxin type A can be produced form the Hall A strain of Clostridium botulinum with characteristics of $3.10^7$ U/mg, an $A_{260}/A_{278}$ of less than 0.60 and a distinct pattern of banding on gel electrophoresis. The known Schantz process can be used to obtain crystalline botulinum toxin type A, as set forth in Schantz, E. J., et al, Properties and use of Botulinum toxin and Other Microbial Neurotoxins in Medicine, *Microbiol Rev.* (1992), 56, 80-99. Generally, the botulinum toxin type A complex can be isolated and purified from an anaerobic fermentation by culturing Clostridium botulinum type A in a suitable medium. The known process can also be used, upon separation out of the non-toxin proteins, to obtain pure botulinum toxins, such as for example: purified botulinum toxintype A with an approximately 150 kD molecular weight with a specific potency of $1\text{-}2.10^8$ $LD_{50}$ U/mg or greater, purified botulinum toxin type B with an approximately 156 kD molecular weight with a specific potency of $1\text{-}2.10^8$ $LD_{50}$ U/mg or greater, and purified botulinum toxin type F with an approximately 155 kD molecular weight with a specific potency of $1\text{-}2.\text{times}.10^7$ $LD_{50}$ U/mg or greater.

Already prepared and purified botulinum toxins and toxin complexes can be obtained from List Biological Laboratories, Inc. (Campbell, Calif., USA); the Centre for Applied Microbiology and Research (Porton Down, UK); Wako (Osaka, Japan), as well as from Sigma Chemicals (St. Louis, Mo., USA).

Botulinum toxin of type A was first used in man in 1981. The first therapeutic uses related to the treatment of certain neuromuscular disorders that include blepharospasm, strabismus and hemifacial spasm. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months.

Spastic bladder treatment by botulinum toxin was first disclosed in U.S. Pat. No. 5,437,291. The method of administration disclosed is the direct injection into the bladder wall.

PCT patent application WO 99/03483 further discloses the use of botulinum toxin for the treatment of various urinary disorders. The administration of toxin consists in an injection in the lateral bladder wall by means of an endoscopic device introduced through the urethra.

The Applicant has now surprisingly found that it is possible to treat patients with urinary disorders and notably spastic bladder without using such an injection. This can be achieved for example by one of the following methods:

infusing the patients' bladder with a liquid or semi-solid formulation of botulinum toxin;

depositing a gel formulation containing botulinum toxin at the appropriate location of the patients' bladder;

spraying a spray formulation containing botulinum toxin at the appropriate location of the patients' bladder; or topically applying a solid (e.g. lyophilised), semi-solid or liquid botulinum toxin formulation that is put or spread on the outer walls of a balloon which is then inflated in the bladder so as to be in contact with said bladder's wall.

By spray formulation is understood in the present application a solid or liquid formulation, that is or can be split into particles or droplets with a mean diameter of less than 1 mm, preferably of less than 500 µm and more preferably less than 100 µm.

The invention therefore relates to the use of a liquid, semi-solid, gel, spray or solid (e.g. lyophilised) formulation of botulinum toxin for the preparation of a medicament intended to treat a disorder characterised by bladder spasms wherein said medicament is for administration by infusion into the bladder or local administration without injection into the bladder wall.

Liquid formulations may in particular be a liquid formulation that is not miscible with water and such that the formulation is less dense than water; an advantage of this execution mode is that the formulation tends to separate and preferentially be in contact with the bladder. The liquid formulations may also be water solutions (e.g. a saline water solution) or suspensions.

Besides, the liquid or semi-solid formulation may be replaced by a gel (including a double gel) or another adhering formulation. This type of formulation will be particularly advantageous as it will allow the selective application of the formulation to the appropriate bladder wall locations, avoiding administration to the trigone.

Alternatively, the formulation may be in the form of a spray containing the botulinum toxin. This spray may notably be created using a two-compartment capsule containing in one compartment botulinum toxin powder and in the other explosives which will bring about the spraying of botulinum toxin once explosion occurs; hence, according to this particular variant, the capsule is first brought at the appropriate location near the bladder wall and then the explosion triggered to spray the botulinum toxin on said wall.

According to a further variant of the invention, a solid (e.g. lyophilised), semi-solid or liquid botulinum toxin formulation may be coated or spread over the outer walls of a balloon. The balloon is brought into the bladder using an endoscopic or cystoscopic apparatus or, more preferably, only a catheter; it is then inflated in the bladder until it is in contact with the bladder walls. In this manner, the botulinum toxin can be delivered at the appropriate bladder wall locations, avoiding administration to the trigone. A further object of the invention is therefore the use of a solid (e.g. lyophilised), semi-solid or liquid botulinum toxin formulation spread on the outer wall of a balloon intended to be inflated inside the bladder for the preparation of a medicament intended to treat a disorder characterised by bladder spasms.

Preferably, the botulinum toxin formulation used for this invention will comprise a penetration enhancer.

To summarise, according to the invention, the formulation of botulinum toxin does not need to be injected but should simply be put in contact with the bladder wall. This mode of administration is much easier for the doctor.

According to this invention, disorders characterised by bladder spasms include notably:

urinary incontinence due to unstable bladder or unstable detrusor sphincter;

voiding complications due to detrusor overactivity or unstable detrusor sphincter;

detrusor sphincter dyssynergia;

urinary retention secondary to spastic sphincter or hypertrophied bladder neck; or neurogenic bladder dysfunction secondary to Parkinson's disease, spinal cord injury, stroke or multiple sclerosis or characterised by a spasm reflex.

In this application, unless stated otherwise, the words "botulinum toxin" always refer to a botulinum toxin complex (made from the toxin and one or more complexing proteins) or a high purity botulinum toxin (botulinum toxin which is substantially free from any complexing protein).

By botulinum toxin complex shall be notably understood the active principles of the products DYSPORT® (registered trademark of the Applicant), BOTOX® (registered trademark of Allergan), VISTABEL® (registered trademark of Allergan), NEUROBLOC® (registered trademark of Elan) or MYOBLOC® (registered trademark of Elan).

By high purity botulinum neurotoxin (type A, B, $C_1$, D, E, F or G) is meant, in the present application, botulinum neurotoxin (type A, B, $C_1$, D, E, F or G) free from complexes including at least another protein. In other words, a high purity botulinum neurotoxin (type A, B, $C_1$, D, E, F or G) does not contain significant quantities of any other *Clostridium* spp derived protein than botulinum neurotoxin (type A, B, $C_1$, D, E, F or G).

Preferably, the invention will be such that the medicament prepared is intended to treat a disorder selected from the group consisting of urinary incontinence, urinary retention and neurogenic bladder dysfunction.

A liquid or semi-solid formulation intended for bladder infusion according to the invention will preferably not have a volume exceeding 100 ml, and more preferably 80 ml. For example, a volume of 20 to 80 ml, and notably a volume of 40 to 60 ml (e.g. about 50 ml), will be appropriate. The same volumes will apply for a gel formulation intended to be deposited in the patient's bladder.

Preferably, the viscosity of the formulation according to the invention will be greater than that of the corresponding water solution thanks to the use of a thickening agent like gelatine, carboxymethyl cellulose, polyethylene glycol, glycerol, mannitol or a surfactant.

Furthermore, liquid formulations used for the invention will preferably be such that they have a viscosity from 0.5 to 500 centipoises, and more preferably from 1 to 500 centipoises. Semi-solid formulations used for the invention will preferably be such that they have a viscosity from 500 to 10,000 centipoises, and more preferably from 2,000 to 10,000 centipoises. Gel formulations used for the invention will preferably be such that they have a viscosity from 10,000 to 100,000 centipoises, and more preferably from 50,000 to 100,000 centipoises.

For use in a bladder infusion, the liquid or semi-solid formulation according to the invention will typically contain from 100 to 2,500 units of botulinum toxin type A or F, or from 4,000 to 50,000 units of botulinum toxin type B or a clinically equivalent amount for other serotypes as is known to the skilled person.

Nevertheless, the dose of botulinum toxin to provide according to the present invention for treatment of the abovementioned diseases or disorders, varies depending on the age and body weight of the subject to be treated, as well as the state of the latter, and will be finally decided by the attending doctor or veterinarian. Such a quantity determined by the attending doctor or veterinarian is here called "therapeutically effective quantity".

For the purposes of the instant patent application, one unit (U) of botulinum toxin is defined as the $LD_{50}$ upon intraperitoneal injection into female Swiss Webster mice weighing 18 to 20 grams each.

Methods of treatment of disorders characterised by bladder spasms comprising the administration by infusion of a liquid, semi-solid or gel composition or spraying a spray composition according to the invention into the bladder of a patient in need thereof are also within the scope of this invention. These methods of treatment can notably be carried out under cystoscope control, but using flexible cystoscopes, mini-cystoscopes or even simple catheters will be preferred. The use of the aforesaid devices can be combined with a radioscopic control, but may also be carried out without any such control.

For the case of a spray formulation, the injection nozzle will preferably have an umbrella or conic shape in order to direct the spray in an appropriate fashion.

According to the instant invention, the infusion or contact with the botulinum toxin formulation should last any time between 10 minutes and 12 hours (overnight).

A preferred execution mode for this invention will involve the use of a balloon whose outer wall is coated with a botulinum toxin formulation, said balloon being intended to be inflated in the bladder of the patient to be treated with the purpose of releasing the toxin into the bladder wall.

The method uses a balloon that can be introduced, through the urethra, into the bladder, that can be inflated in the bladder in order to enter in contact with the bladder wall and that can also be deflated afterwards. The surface of the balloon is previously covered by a botulinum toxin formulation in order to, later, transfer said formulation as a layer between balloon and bladder wall.

The botulinum toxin formulation can be liquid, semisolid or solid and can optionally comprise one or more penetration enhancers to favour the botulinum toxin transfer from the surface to the target of the drug.

The balloon is the transfer-target device and can play an occlusive role or any other mechanical functions likely to increase botulinum toxin penetration thanks to the process and/or to the balloon surface, composition, etc.

One of the preferred device presentations is the one used in balloon angioplasty. However, the skilled person may contemplate any other where an inflated balloon is used in order to enter in contact with the bladder wall to ensure botulinum toxin penetration into the bladder wall.

Hence, as for angioplasty, the device will preferably be thin and long for transluminal access to the bladder, the diameter and length being adapted to urethra and bladder. The deflated total diameter of the balloon could be less than 1 cm and preferably less than 5 mm and the deflated total length less than 15 cm and preferably less than 10 or even 5 cm.

The balloon device could come with a control guide wire and/or a peripheral guide catheter. For example, a thin and flexible balloon catheter can be positioned at rest in a reservoir and when necessary expelled from the catheter (optionally through a catheter guide), leaving the balloon to expand gently into the bladder.

One may monitor the progress of the treatment on an X-ray machine thanks to the metallic guide wire but it can also be contemplated that the wire is used as a guide to determine the appropriate position with contact on top of the bladder before treatment application without any radiographic need, thus making the treatment even simpler to perform. The device shape and working process can be made in a way to offer contact in the target area and for instance avoiding balloon contact in the trigone or urethra area.

According to the invention method, the balloon's outer surface is to be covered with the botulinum toxin formulation to be delivered.

Different approaches with solid, semi-solid or liquid compositions of the drug can be contemplated as detailed hereafter.

For solid formulations, one can prepare concentrated liquid aqueous or organic solutions of botulinum toxin, to wet the deflated balloon in these solutions of the drug and to dry or freeze-dry the preparation in order to obtain a solid layer of the drug on top of the surface. If necessary, only one defined part of the balloon's surface could enter in contact with the solution and then be covered by the drug. It can also be contemplated to add one or more excipients likely to enhance drying and/or penetration of the toxin. For instance, alcoholic solutions and/or pH preparations can be used to obtain local inflammation, creating micro-lesions that will ease the transfer of the toxin through the epithelium layer. Besides, surfactant or organic solvents can be incorporated into the toxin formulation to improve the delivery. In the end, aqueous medium and/or local humidity in the bladder could rehydrate the solid composition and give the pH, concentration and liquid vehicle to transfer the toxin.

Semi-solid or gel like compositions could also be used with the balloon device. Here also one can wet the balloon surface in a botulinum toxin gel preparation or semi-solid formulation to obtain the botulinum toxin coating layer. The treatment could also be realised just by putting on top of the balloon in the guide catheter the semi-solid or gel preparation. During the process, this layer will cover the balloon's surface as a result of the balloon inflation and then be trapped, stuck and squeezed between the balloon and the bladder wall.

A liquid preparation could also be used with the device. This preparation can be already associated with the device as a layer on a deflated balloon or a liquid reservoir in the tip of the guide catheter. The liquid reservoir at the tip of the guide catheter may as well be filled using a syringe just before use with a high aqueous concentration of botulinum toxin in a small volume (e.g. 500 units of DYSPORT® in 0.5 ml or less of saline solution); pH modifying agents, organic solvents, viscosity and penetration enhancers may be added if necessary. This tip part will wet the balloon as it is pushed out of the guide catheter and cover it when it inflates in the bladder, allowing the toxin composition to enter in contact with the bladder wall.

Various methods of treatment can be contemplated thanks to the invention's balloon device.

For example, the balloon can be inflated and deflated several times, with a contact between the balloon's outer wall and the bladder inner wall being maintained for a certain time in between. The contact time will be chosen for optimising penetration (in general less than one hour, for instance 10 minutes) as well as the number of times the balloon will be inflated.

The pressure exerted on the bladder wall could also play a favorable plastic and penetration role. It will therefore be adapted by the treating physician to each patient. The balloon can be inflated to a relatively high pressure that can be precisely controlled (as it is normally prevented from blowing up thanks to the bladder wall). In addition, the device can be inflated or deflated several times during treatment and one can perform some pressure jerks to improve toxin penetration.

Depending on the treatment conditions, the botulinum toxin administration using the balloon dilatation on the tip of the catheter works thanks to an occlusive phenomenon only or thanks to both an occlusive phenomenon and the pressure exerted by the balloon on the bladder wall.

After treatment, the balloon is deflated and withdrawn just by removing the catheter and/or guide wire.

If by chance the bladder wall gets damaged because of treatment, the healing would have the time it needs as treatments could be spaced by time intervals of 6 months or more as the toxin is effective for that duration when treating bladder disorders.

Other execution modes of the balloon device according to this invention include having on the balloon surface rough patches to improve botulinum toxin penetration. Those sharp elements can be incorporated, similarly to coronary stents, on the balloon.

It could also be contemplated to use an elastic catheter tipped with a balloon as a way to target local multi-injections, similarly to what is described for example in U.S. Pat. No. 6,638,246. According to this variant, the balloon would be fitted with small needles (e.g. microneedles of about 1 mm length and about 130 µm diameter) that would be attached and folded safely into the balloon's surface. As the balloon is inflated, the microneedle would penetrate the bladder wall and the botulinum toxin formulation would be injected.

The execution modes wherein the balloon is fitted with rough patches or microneedles present the advantage of allowing targeted administration of the botulinum toxin formulation into defined areas of the patient's bladder.

Thanks to this balloon device, the treatment dose can be accurate, already fixed and associated to the device or easily selected and prepared by the physician using standard procedures for liquid injections.

It should be mentioned that the balloon system previously described can be used for any kind of active substance that can be formulated as a solid, semi-solid or liquid pharmaceutical composition and that can be delivered through an epithelium surface into an accessible body reservoir or vessel like for example the bladder, the colon, the bowel, the stomach, the oesophagus, the nose, the sinus, the ear, the eye or the blood vessels (veins or arteries).

Possible uses of this balloon device therefore include for example:
    introducing the invention balloon coated with an anti-restenosic drug, an antithrombogenic agent, an endothelialisation promoter, a radioactive isotope, a platelet antiaggregant agent, a fibrinolytic agent, an anti-inflammatory agent, an antiproliferation agent, a radio opaque substance, a gene therapy agent, an inhibitor and/or promoter of cellular adhesion and/or growth (e.g. somatostatin analogues like lanreotide or octreotide, glucocorticoids, glycerol, heparin, botulinum toxin, a cytotoxic agent, a cytostatic agent, etc.) into the appropriate artery locations and inflating it to release said drug, agent, inhibitor or promoter;
    introducing the invention balloon coated with an anti-ulcer drug (e.g. omeprazole, esomeprazole or the like) into the stomach and inflating it to release said anti-ulcer drug; or
    introducing the invention balloon coated with an anti-inflammation drug into the colon, bladder or bowel and inflating it to release said anti-inflammation drug.

Of course, the various general improvements indicated for botulinum toxin formulations to be used on balloons according to this invention (such as, among many other things, the use of penetration enhancers) apply mutatis mutandis to the corresponding other drug formulations.

The term "about" refers to an interval around the considered value. As used in this patent application, "about X" means an interval from X minus 10% of X to X plus 10% of X, and preferably an interval from X minus 5% of X to X plus 5% of X.

Unless they are defined differently, all the technical and scientific terms used here have the same meaning as that usually understood by an ordinary specialist in the field to which this invention belongs. Similarly, all publications, patent applications, all patents and all other references mentioned here are incorporated by way of reference.

The following example is presented to illustrate the above and must in no case be considered as a limit to the scope of the invention.

EXAMPLE

A woman in her sixties suffers from urinary incontinence due to unstable bladder. She is infused in the bladder, through a catheter introduced into the urethra and the bladder and with the assistance of an endoscope apparatus, with 50 ml of a physiological saline solution containing 2,000 units of botulinum toxin type A (DYSPORT®; supplier: Ipsen Ltd, Wrexham, UK).

Pharmacological Procedures
Bladder Function

The bladder capacity (in ml) is measured in patients before and after treatment at regular time intervals for up to 12 months. Additionally voiding function is recorded over this period.

The invention claimed is:
1. A method of treating a bladder spasm disorder in a patient comprising administering an effective amount of botulinum toxin to a patient in need thereof, the method comprising spreading a solid, semi-solid or liquid formulation of botulinum toxin onto an outer wall of a balloon; inserting the balloon into the bladder of the patient; and, contacting the wall of the bladder by inflating the balloon.

2. The method according to claim 1, wherein the bladder spasm disorder is selected from the group consisting of urinary incontinence due to unstable bladder of unstable detrusor sphincter, voiding complications due to detrusor overactivity of unstable detrusor sphincter, urinary retention secondary to spastic sphincter of hypertrophied bladder neck and neurogenic bladder dysfunction secondary to Parkinson's disease, spinal cord injury, stroke or multiple sclerosis.

3. The method according to claim 1, wherein the liquid or semi-solid formulation of botulinum toxin has a volume of 20 to 80 ml.

4. The method according to claim 1, wherein the liquid or semi-solid formulation of botulinum toxin contains from 100 to 2500 units of botulinum toxin type A.

5. The method according to claim 1, wherein the liquid or semi-solid formulation contains from 4,000 to 50,000 units of botulinum toxin type B.

6. The method according to claim 1, wherein the semi-solid formulation is in the form of a gel formulation.

7. The method according to claim 1, wherein the formulation is in the form of a spray formulation.

8. The method of treatment according to claim 1, wherein the disorder is urinary incontinence due to unstable bladder, the formulation is in the form of semi-solid formulation, and the botulinum toxin is botulinum toxin type A.

9. The method according to claim 1, wherein the bladder spasm disorder is voiding complications due to detrusor overactivity or unstable detrusor sphincter.

* * * * *